United States Patent [19]

Caesar et al.

[11] 4,083,889
[45] Apr. 11, 1978

[54] PROCESS FOR MANUFACTURING ETHYLENE

[75] Inventors: Philip Dornin Caesar, Princeton; Roger Allen Morrison, West Deptford, both of N.J.

[73] Assignee: Mobil Oil Corporation, New York, N.Y.

[21] Appl. No.: 800,754

[22] Filed: May 26, 1977

[51] Int. Cl.² .................. C07C 1/24; C07C 11/04; C07C 43/04; B01J 29/28
[52] U.S. Cl. .................. 260/682; 260/614 R
[58] Field of Search ......................... 260/682

[56] References Cited

U.S. PATENT DOCUMENTS

| | | | |
|---|---|---|---|
| 3,702,886 | 11/1972 | Argaver et al. | 423/328 |
| 3,709,979 | 1/1973 | Chu | 423/328 |
| 3,832,449 | 8/1974 | Rosinski et al. | 423/328 |
| 3,894,106 | 7/1975 | Chang et al. | 260/668 R |
| 3,931,349 | 1/1976 | Kuo | 260/668 R |
| 4,016,245 | 4/1977 | Plank et al. | 423/328 |
| 4,025,571 | 5/1977 | Lago | 260/668 D |
| 4,025,575 | 5/1977 | Chang et al. | 260/682 |
| 4,046,859 | 9/1977 | Plank et al. | 423/328 |
| 4,058,576 | 11/1977 | Chang et al. | 260/673 |

FOREIGN PATENT DOCUMENTS 1,165,479  10/1969  United Kingdom ......... 260/682

*Primary Examiner*—Delbert E. Gantz
*Assistant Examiner*—G. E. Schmitkons
*Attorney, Agent, or Firm*—Charles A. Huggett; Vincent J. Frilette

[57] ABSTRACT

Ethylene is produced by catalytic conversion of a methanol feed in the presence of steam or water diluent. The catalyst employed is exemplified by HZSM-5, a crystalline aluminosilicate zeolite, and the conversion is conducted at relatively low temperature, i.e. from about 600° F to about 750° F. The hydrocarbon conversion product contains at least 18 wt.% ethylene.

8 Claims, 1 Drawing Figure

PROCESS FOR MANUFACTURING ETHYLENE

BACKGROUND OF THE INVENTION

1. Field of the Invention

This invention is concerned with the manufacture of ethylene from a methanol feed. It is particularly concerned with the catalytic conversion of a methanol feed to a hydrocarbon mixture of high ethylene content.

2. Description of the Prior Art

A remarkable growth in the production of synthetic fibers, plastics and petrochemicals has taken place in recent decades. This growth, to a very large extent, has been supported and encouraged by an expanding supply of inexpensive petrochemical raw materials such as ethylene, propylene, and other lower olefins. The principal raw material for ethylene at the present time is petroleum naphtha, which is steam cracked to produce a mixture of products from which ethylene is recovered. A large fraction of this ethylene is used in the manufacture of polyethylene and styrene monomer.

The burgeoning demand for olefins has of course led to periods of shortage, due either to short supply of suitable petroleum feedstocks or to limited processing capacity. It is obviously desirable to provide efficient means for manufacturing ethylene from raw materials other then petroleum.

U.S. Pat. No. 4,025,575, Ser. No. 566,166 filed Apr. 8, 1975 describes a process by which lower alcohols and/or their ethers are converted to a mixture of $C_2$ to $C_5$ olefins by contact at subatmospheric inlet partial pressure with a crystalline aluminosilicate zeolite catalyst having a constraint index of 1 to 12 and a silica to alumina ratio of at least 12.

The production of olefins from aliphatic ethers by catalytic conversion with, e.g., a HZSM-5 zeolite catalyst is described in U.S. Pat. No. 3,894,106 issued July 8, 1975.

The use of diluents to dissipate exothermic heat in a two stage conversion of methanol to gasoline is described in U.S. Pat. No. 3,931,349 issued Jan. 6, 1976.

A two stage conversion of a lower alcohol to olefins or to gasoline, which process employs a tubular reactor for the second stage is described in U.S. Pat. No. 4,058,576, Ser. No. 720,870 filed Sept. 7, 1976.

BRIEF SUMMARY OF THE INVENTION

It has now been discovered that a methanol feed is directly converted to a hydrocarbon mixture of high ethylene content by catalytic contact of the feed in the presence of 2 to 20 mols of steam diluent per mol of feed, said contact being effected at a temperature from about 600° F to about 750° F, with a zeolite catalyst such as HZSM-5, said zeolite catalyst being more fully described hereinbelow. As will be seen, the presence of the steam diluent induces sustained high catalytic activity with high selectivity for the formation of ethylene even at high conversion levels.

The process of this invention, more fully described hereinbelow, produces as the primary product a mixture comprising hydrocarbons, and in its preferred form, the ethylene content of the hydrocarbon is at least about 18 wt.%. Since the methanol feed may be manufactured from synthesis gas, i.e. a mixture of CO and $H_2$ made from coal or from natural gas, this invention provides a process for making ethylene which is independent of petroleum feedstocks.

It is to be noted that by the process of this invention the methanol feed, which is a one carbon alcohol, produces olefins which contain at least 2 carbon atoms. Thus, the conversion of this invention clearly differs from the classical dehydration of alcohols in which the olefin produced has the same number of carbon atoms as the alcohol which is charged.

DETAILED DESCRIPTION OF THE INVENTION

Figure 1:
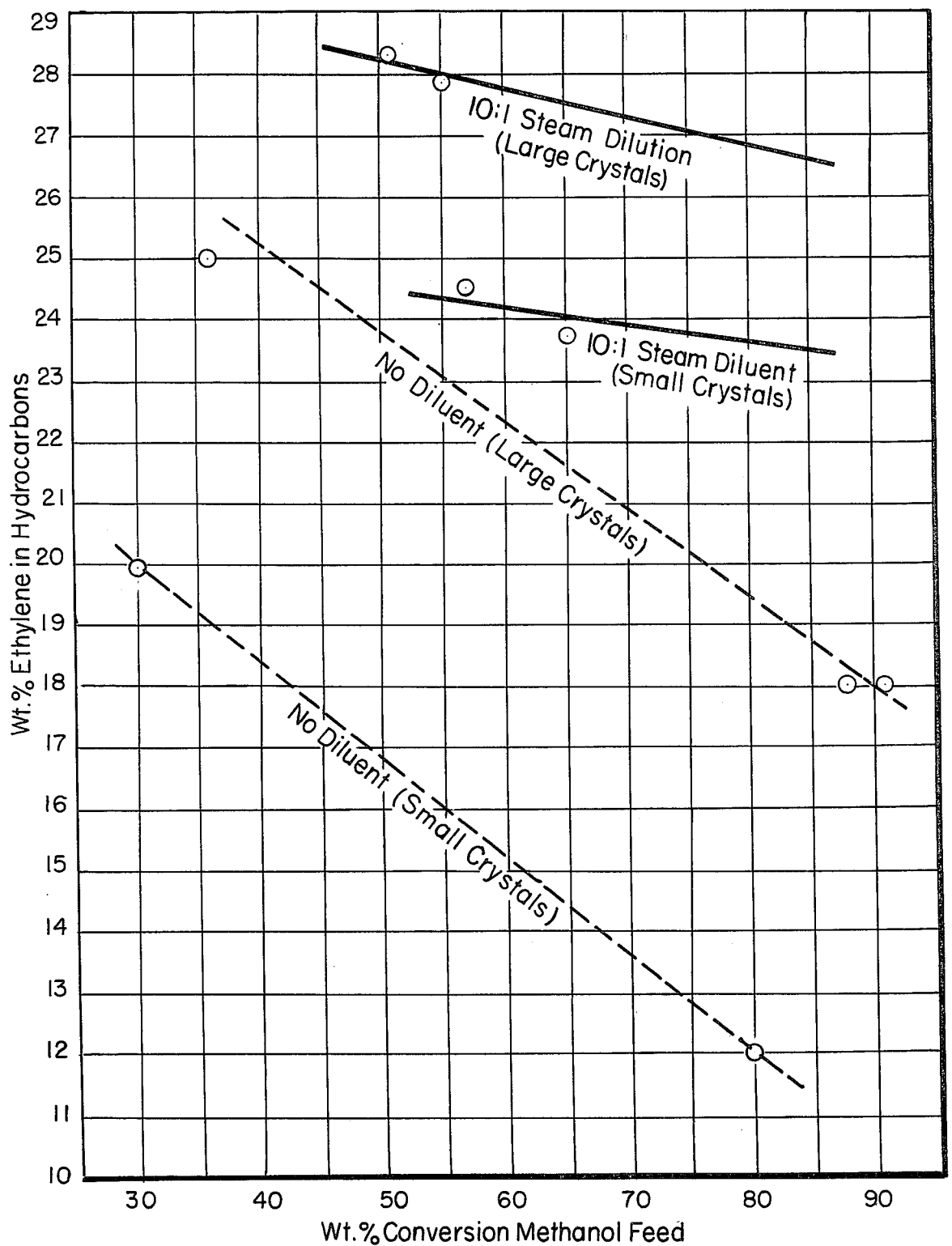
FIG. 1 illustrates effect of steam diluent on selective formation of ethylene.

Before proceeding with the detailed description of this invention, it should be noted that the term "methanol feed" as used in this invention designates only the organic material used as feed, i.e. the organic compounds subjected to catalytic conversion to olefins. Since methanol is miscible with water, the charge to the catalytic reaction zone may actually contain large amounts of water, but only the methanol with associated organic compounds constitutes the methanol feed, the water providing a portion or all of the steam diluent. Thus, all computable quantities referred to methanol feed, such as composition and weight hourly space velocity (WHSV), for purposes of the present invention are to be computed on a substantially anhydrous basis.

Any composition comprising at least 60 wt.% of methanol may be used as methanol feed in this invention. Substantially pure methaol, such as industrial grade anhydrous methanol, is eminently suitable. Crude methanol, which usually contains from 12 to 20 wt.% water, or more dilute solutions, also may be used. Small amounts of impurities such as higher alcohols, aldehydes, or other oxygenated compounds in the methanol feed have little effect on the conversion of this invention. The methanol feed may contain minor amounts of dimethyl ether. When this component is present, it is preferred that it constitute not more than about 20 wt.% of the total feed. For purposes of the present invention, it is contemplated to directly convert methanol to a hydrocarbon mixture characterized by a high content of ethylene. Such amounts of dimethyl ether as may be formed concomitantly in the conversion, however, may be recovered and recycled with fresh methanol feed, and the dimethyl ether content calculated on the total of recycle and fresh feed will not ordinarily exceed the above-noted 20 wt.%.

To achieve the high selectivity for the formation of ethylene, the methanol feed is contacted with the hereinbelow described crystalline aluminosilicate zeolite catalyst in the presence of 2 to 20 mols, and preferably 3 to 10 mols, of steam per mol of methanol feed, said contacting being effected at the conditions hereinafter described. The steam diluent may be provided directly by injecting the requisite amount of water or steam into the reaction zone; or it may be provided totally or in part by water mixed with the methanol feed, it being understood that the water forms steam in the reaction zone at the prescribed reaction conditions.

In the practice of this invention, the steam diluent may be supplemented with an inert diluent selected from the group consisting of hydrogen, helium, nitrogen, carbon dioxide, a $C_1$ to $C_7$ hydrocarbon and flue gas. In such a case, up to 20 total mols of steam plus inert diluent may be used.

The catalyst composition useful in this invention consists essentially of a crystalline aluminosilicate zeolite characterized by a silica to alumina mol ratio of at least 12 and a "constraint index" of from about 1 to about 12, said constraint index being defined with particularity hereinbelow. Non-limiting examples of said crystalline aluminosilicate zeolite include ZSM-5, ZSM-11, ZSM-12, ZSM-35, ZSM-38 and ZSM-41.

The synthesis and characteristics of zeolite ZSM-5 are described in U.S. Pat. No. 3,702,886 issued Nov. 14, 1972, the disclosure of which is incorporated herein by reference. As synthesized and prior to base exchange and activation, the zeolite ZSM-5 of the catalyst composition useful in this invention has a formula, in terms of mol ratios of oxides in anhydrous state, as follows:

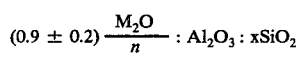

wherein M is selected from the group consisting of a mixture of alkali metal cations, especially sodium, and tetraalkylammonium cations, the alkyl groups of which preferably contain 2 to 5 carbon atoms, and $x$ is at least 5. Particularly preferred is a zeolite having the formula in the anhydrous state as follows:

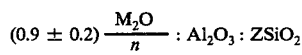

wherein Z is from greater than 30 to about 350 or higher.

The synthesis and characteristics of zeolite ZSM-11 are described in U.S. Pat. No. 3,709,979 issued Jan. 9, 1973, the disclosure of which is incorporated herein by reference.

The synthesis and characteristics of zeolite ZSM-12 are described in U.S. Pat. No. 3,832,449, issued Aug. 27, 1974, the disclosure of which is incorporated herein by reference.

The synthesis and characteristics of ZSM-35 are described in U.S. Pat. No. 4,016,245 issued Apr. 5, 1977, the disclosure of which is incorporated herein by reference.

The synthesis and characteristics of ZSM-38 are described in U.S. Pat. No. 4,046,859, Ser. No. 560,412, filed Mar. 20, 1975, the entire contents of which are herein incorporated by reference.

The synthesis and characteristics of ZSM-41 are described in U.S. Application Ser. No. 813,406 filed July 5, 1977, herein incorporated by reference.

Certain preparation techniques result in particularly large crystallite size aluminosilicate zeolites. These large crystal-size varieties of ZSM-5, ZSM-11, etc. are preferred as the crystalline aluminosilicate component of the catalyst composition used in this invention. A method of preparation is described in U.S. Application Ser. No. 784,497 filed Apr. 4, 1977, herein incorporated by reference.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms, or, if elliptical in pore shape, at least the size of the pores in ZSM-5. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are:

| Crystalline Aluminosilicate | CI |
|---|---|
| ZSM-5 | 8.3 |
| ZSM-11 | 8.7 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possibly occluded contaminants aned binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F to 950° F, the constraint index will have a value for any given zeolite of interest herein within the approximate range of 1 to 12.

The specified zeolites described, when prepared in the presence of organic cations, are catalytically inactive, possibly because the intracrystalline free space is occupied by organic cations from the forming solution. They may be activated by heating, for example, in an inert atmosphere at 1000° F for 1 hour, followed by base exchange with ammonium salts and by calcination at 1000° F in air. The presence of organic cations in the forming solution may not be absolutely essential to the formation of this type zeolite; however, the presence of these cations does appear to favor the formation of this special type of zeolite. More generally, it is desirable to active this type catalyst by base exchange with ammonium salts followed by calcination in air at about 1000° F for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates as ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, Apr. 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal, or in mercury under pressure (mercury porosimeter). It is possible that the unusual sustained activity and stability of this class of zeolite is associated with its high crystal anionic framework density of not less than about 16 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The catalyst composition useful in this invention may be in the form of compacted pellets, or extrudate particles with a diameter, for example, 150 inch or ¼ inch; or in the form of beads; or in the form of fine particles of about 50 microns diameter suitable for fluidization. The particular form chosen is determined by the type of catalyst bed to be used, which may be a fixed compact bed, a fixed fluidized bed, or a variety of transport bed. In any case, the crystalline aluminosilicate zeolite component of the catalyst composition may be blended with a binder such as alumina or silica alumina to form the above-described particles by methods well known to those skilled in the art of catalyst preparation. As noted above, the specific zeolites useful in the catalyst compositions of this invention may require activation by base exchange with ammonium salts and calcination in air. These steps may be done before or after pelletizing or extruding to form the desired catalyst particles. Regardless of when these steps are effected, the catalyst composition useful in this invention consists essentially of a crystalline aluminosilicate zeolite having the above-described characteristics and at least partially in the hydrogen form. Of the enumerated zeolites, HZSM-5, which is in the hydrogen form, is preferred. Particularly preferred because of its enhanced effectiveness is HZSM-5 having a crystallite size greater than about 0.5 microns, said crystallite size referring to a weighted average.

The methanol feed is passed over the catalyst at a rate of 0.2–20 WHSV (weight hourly space velocity), preferably at 0.5 to 5.0 WHSV. In all cases, the WHSV is calculated on the pounds of methanol fed per hour per volume of catalyst. For purposes of this invention, the methanol feed and diluent are contacted with the catalyst at a pressure of 1 to 10 atmospheres absolute, i.e. at a pressure of 0 to 135 p.s.i.g. (pounds per square inch gauge). It is preferred, however, to conduct the reaction at from about 0 to about 50 p.s.i.g. It is important for purposes of this invention to maintain the reaction temperature as low as is consistent with the desired conversion per pass, this temperature being maintained at about 600° to 750° F, and preferably within the range of about 600° F to about 700° F. Temperatures referred to herein are to be understood to refer to the maximum temperature within the reaction zone. Thus, in a fixed-bed operation, the inlet temperature may be lower than 600° F. Within the prescribed conditions, a conversion per pass of from 40 to about 90% of the methanol is achieved and the hydrocarbon mixture formed contains at least 18 wt.% ethylene.

The term "conversion", as used herein, is to be understood to mean a chemical change in which a hydrocarbon having at least 2 carbon atoms is formed. Thus, a substantially pure methanol feed will form a hydrocarbon mixture and also some dimethyl ether. This dimethyl ether is ignored in computing conversion since no new carbon to carbon bonds form in its formation. If some dimethyl ether is present in the methanol feed, its conversion to hydrocarbons is added to that of the methanol to arrive at a "conversion" value. Specifically, 50% conversion as used herein means that 50% of the total —CH$_2$— groups present in the methanol and dimethyl ether of the methanol feed is converted to hydrocarbons.

The effect of diluent as used in this invention is evident from an inspection of FIG. 1. With HZSM-5 catalyst in which the crystallite size is less than about 0.5 microns, the ethylene content of the hydrocarbons produced is greater than 18 wt.% at conversion levels from 40 to about 90% with a 10:1 mol ratio of diluent to methanol feed. In the absence of diluent, the ethylene content of the hydrocarbons produced falls rapidly to as little as 12 wt.% at 80% conversion. With HZSM-5 catalyst in which the crystallite size is greater than about 0.5 microns, the ethylene content is always above 21 wt.% of the hydrocarbons formed, and again a rapid decline with increased conversion is observed in the absence of diluent. Thus, whereas in all cases the practice of the present invention results in a hydrocarbon mixture that contains at least 18 wt.% ethylene and improved aging behavior with time on stream, the ethylene content may be considerably higher than 18% if the large crystallite size catalyst is used, or if some other modification of the crystalline aluminosilicate zeolite is used in which the diffusional characteristics are moderated by means other than forming large crystals. It has been observed, for example, that silica-coated HZSM-5 also produces unusually high ethylene yields, and again the advantage of cofeeding steam diluent as taught in the present invention is a further increase in selectivity for ethylene. Thus, while the hydrocarbon mixture contains at least 18 wt.% ethylene in all cases contemplated as within the scope of the process of this invention, in a particularly preferred mode of operation the concentration of diluent, temperature, space velocity (WHSV), pressure and conversion level are so selected from the hereinabove prescribed ranges that the hydrocarbon mixture produced contains at least 1.5 wt.% more ethylene than is produced in the absence of diluent, and under the same reaction conditions.

After the catalyst has been on stream for sufficient time to accumulate inactivating deposits and is no longer effective, its activity may be restored by contact with oxygen-containing gas at sufficiently elevated temperature to burn away the deposits.

The hydrocarbon mixture produced by the process of this invention is recovered and the ethylene may be concentrated or separated by distillation or other techniques well understood in the art.

The following examples are given only for the purpose of illustration, and are not to be construed as limiting in any way.

EXAMPLES 1 – 3

HZSM-5 crystalline aluminosilicate zeolite catalyst with a crystallite size less than 0.5 microns was mixed with alumina binder and extruded to form cylindrical pellets. The catalyst was charged to a reactor and pure methanol was fed over it together with substantially inert diluent or steam, as specified. The results of comparing substantially anhydrous with steam diluent are shown in Table I.

TABLE I

| | Example No. | | |
|---|---|---|---|
| | 1 | 2 | 3 |
| Temperature, ° F | 633 | 633 | 644 |
| Diluent, (mol ratio) | (10:1)helium | (10:1)steam | (10:1)steam |
| WHSV (methanol) | 1.0 | 1.0 | 1.0 |
| Conversion, % | 100 | 64.9 | 70.6 |
| Wt.% ethylene in hydrocarbons | 7.2 | 24.5 | 22.7 |

U.S. Patent Application 800,753 filed on even date herewith describes the use of substantially anhydrous diluent in a process for making ethylene from methanol.

What is claimed is:

1. In a method for producing a hydrocarbon mixture rich in olefins by contacting a methanol feed and a diluent with a catalyst comprising a crystalline aluminosilicate zeolite having a constraint index of 1.0 to 12.0, a silica to alumina ratio of at least about 12 and a dried crystal density in the hydrogen form of not substantially less than 1.6 grams per cubic centimeter, said contacting being effected under conversion conditions, the improvement, whereby increasing the ethylene content of said hydrocarbon mixture, which comprises:

contacting said methanol feed with said zeolite catalyst at a temperature of about 600° F to about 750° F, at a WHSV of methanol of 0.2–20, at a pressure of 0 to 135 p.s.i.g., said contacting being effected in the presence of 2 to 20 mols of steam per mol of methanol feed; and converting from about 40 wt.% to about 90 wt.% of said methanol feed to said hydrocarbon mixture having an increased ethylene content.

2. The improved method claimed in claim 1 wherein said hydrocarbon mixture of increased ethylene content contains at least 18 wt.% ethylene.

3. The improved method claimed in claim 2 wherein said ethylene content is also at least 1.5 wt.% higher than obtained in the absence of said diluent.

4. The improved method claimed in claim 2 wherein said crystalline aluminosilicate zeolite is HZSM-5.

5. The improved method claimed in claim 4 wherein said HZSM-5 has a crystallite size greater than about 0.5 micron.

6. The improved method of claim 4 wherein said hydrocarbon mixture of increased ethylene content contains at least 18 wt.% ethylene, and at least 1.5 wt.% more ethylene than obtained in the absence of said diluent.

7. The improved method of claim 4 wherein said HZSM-5 is silica-coated.

8. The improved method of claim 2 wherein said contacting is effected in the presence of up to 20 mols of diluent, said diluent consisting of 3 to 10 mols of steam per mol of methanol feed supplemented with an inert diluent.

* * * * *

UNITED STATES PATENT AND TRADEMARK OFFICE
CERTIFICATE OF CORRECTION

PATENT NO. : 4,083,889
DATED : April 11, 1978
INVENTOR(S) : PHILIP DORNIN CAESAR and ROGER ALLEN MORRISON It is certified that error appears in the above–identified patent and that said Letters Patent are hereby corrected as shown below:

Column 2, line 31   "methaol" should be -- methanol --

Column 5, line 68   "active" should be -- activate --

Column 6, line 10   "as" should be -- are --

Column 6, line 67   "150 inch" should be -- 1/8 inch --

Signed and Sealed this

Third Day of October 1978

[SEAL]

Attest:

RUTH C. MASON
Attesting Officer

DONALD W. BANNER
Commissioner of Patents and Trademarks